US012741153B2

(12) United States Patent
Dial

(10) Patent No.: US 12,741,153 B2
(45) Date of Patent: Sep. 22, 2026

(54) RESONATOR SYSTEM AND METHOD FOR PULSED ELECTROMAGNETIC FIELD THERAPY

(71) Applicant: DCD TECHNOLOGIES LLC, Ocean Springs, MS (US)

(72) Inventor: Daniel Christopher Dial, Shelton, WA (US)

(73) Assignee: DCD TECHNOLOGIES LLC, Ocean Springs, MS (US)

( * ) Notice: Subject to any disclaimer, the term of this patent is extended or adjusted under 35 U.S.C. 154(b) by 672 days.

(21) Appl. No.: 18/196,966

(22) Filed: May 12, 2023

(65) Prior Publication Data

US 2024/0374909 A1 Nov. 14, 2024

(51) Int. Cl.
*A61N 2/00* (2006.01)

(52) U.S. Cl.
CPC .................................... *A61N 2/00* (2013.01)

(58) Field of Classification Search
CPC ................................................ A61N 2/00-12
See application file for complete search history.

*Primary Examiner* — Thaddeus B Cox
(74) *Attorney, Agent, or Firm* — CHRISTOPHER C. DREMANN, P.C.; Christopher C. Dremann

(57) ABSTRACT

An analog resonator system for generating electromagnetic energy includes a capacitor assembly and a power transformer for supplying electrical potential to the capacitor assembly. The capacitor assembly includes a first capacitor plate, a second capacitor plate and a dielectric insulator plate. The capacitor plates are formed from a first conductive metal material and from a second conductive metal material dissimilar from the first conductive metal material. An analog PEMF therapy device includes the analog resonator system, a bulb electrically connected between the capacitor assembly and the power transformer, and a base electrically connected between the capacitor assembly and the power transformer. A method for analog PEMF therapy includes providing the analog resonator system, supplying electrical potential from the power transformer, electrically connecting the analog PEMF therapy device between the capacitor assembly and the power transformer, and producing continuous, randomized analog wave forms of the electromagnetic energy for the therapy device.

20 Claims, 6 Drawing Sheets

RESONATOR SYSTEM AND METHOD FOR PULSED ELECTROMAGNETIC FIELD THERAPY

FIELD OF THE INVENTION

The present invention relates generally to apparatus, systems, methods and devices for Pulsed Electromagnetic Field (PEMF) therapy. More particularly, the invention is analog resonator system and method configured for analog PEMF therapy and analog PEMF therapy devices. In an exemplary embodiment, the invention is an analog wave form resonance transformer, analog resonator or analog resonator system including a bi-metallic capacitor assembly and a power transformer.

BACKGROUND OF THE INVENTION

Pulsed Electromagnetic Field (PEMF) therapy is a drug-free, non-invasive, holistic modality for enhancing health and wellness. PEMF therapy can reduce pain, inflammation and fatigue by increasing circulation and mobility. Electromagnetic energy is induced into a subject combined with the natural electromagnetic energy of the human body and thereby stimulating a positive response. The body's electromagnetic energy works to increase electrolytes and ions to naturally influence electrical changes on a cellular level and stimulate cellular metabolism. More particularly, the body's electromagnetic energy oscillates the subatomic structure of the cell to increase its energy field, which charges the total molecular structure of the cell, and thereby increases the potential field size of the cell. The increased energy field size requires the cell molecule to become more precise in order to fit within the space available for the cell. The more precise cell molecule enhances the sense of timing between cell components such that proper synchronous activity in the cell improves energy transfer between its cell components and with the cell components of other cells.

Conventional resonance transformers for PEMF therapy typically utilize digitally pulsed synthesizers to generate electromagnetic energy of discrete wave forms. A problem with the digitally pulsed type of PEMF therapy devices is that they produce only a limited operating range of discrete frequencies. The digital electromagnetic energy consists of square wave forms that are turned on and turned off in rapid fire succession causing sharp fluctuations in the electromagnetic energy. Consequently, over time the human body tends to reject the digital electromagnetic energy pulses, making digitally pulsed PEMF therapy a hit and miss proposition.

In addition to being less effective, PEMF therapy devices utilizing digital resonance transformers are susceptible to more serious deficiencies. Digital PEMF therapy devices tend to irritate due to the rapid on and off of the digital pulse waves. Most digital PEMF therapy devices require a particular frequency to be dialed in limiting the range of frequencies produced at one time, thus limiting the body's choice of available frequencies. In addition, many of the existing digital and analog PEMF therapy devices require extensive periodic cleaning, service, repair or replacement.

In view of the foregoing, it is apparent a need exists for a resonator system that overcomes the problems and deficiencies associated with digitally pulsed resonators for PEMF therapy that generate electromagnetic energy of discrete wave forms. A particular need exists for a resonator system that generates a wide spectrum of continuous, randomized electromagnetic energy wave forms. A further particular need exists for an analog resonance transformer, analog resonator or analog resonator system configured for use with analog PEMF therapy devices that avoids irritation, provides a broader range of frequencies that allow for each body to utilize the frequencies it requires. A still further need exists for an analog resonator system that does not require extensive periodic cleaning, service, repair or replacement.

SUMMARY OF THE INVENTION

In one aspect, the present invention is embodied by an analog resonator system for generating pulsed analog wave forms of electromagnetic energy. The resonator system includes a capacitor assembly and a power transformer for supplying electrical potential to the capacitor assembly. The capacitor assembly includes a first capacitor plate and a second capacitor plate that are disposed between and separated by a dielectric insulator plate. The first capacitor plate and the second capacitor plate are each electrically connected to the power transformer. The first capacitor plate is formed from a first metal material and the second capacitor plate is formed from a second metal material that is dissimilar from the first metal material.

In one embodiment of the analog resonator system, the first capacitor plate of the capacitor assembly is formed of a copper (Cu) material and the second capacitor plate of the capacitor assembly is formed of an aluminum (Al) material.

In another embodiment, the capacitor assembly and the power transformer produce continuous analog wave forms of the pulsed electromagnetic energy generated by the resonator system.

In another embodiment, the power transformer is a neon sign transformer for supplying from about 12,000 volts to about 15,000 volts of the electrical potential to the capacitor assembly.

In one embodiment, the analog resonator system further includes a fan for providing forced cooling air to the capacitor assembly, and the capacitor assembly further includes at least one cooling air duct for directing the cooling air to the first capacitor plate and/or to the second capacitor plate.

In another embodiment, the capacitor assembly includes a first housing for containing the capacitor assembly and the analog resonator system includes a second housing for containing the capacitor assembly and the power transformer.

In another embodiment, the first housing of the capacitor assembly is removably contained within the second housing of the analog resonator system.

In another embodiment, the analog resonator system includes a first output terminal and a second output terminal. The first output terminal is electrically connected between the power transformer and the first capacitor plate. The second output terminal is electrically connected between the power transformer and the second capacitor plate.

In another embodiment, the capacitor assembly includes a first capacitor plate terminal that is electrically connected to the first capacitor plate and a second capacitor plate terminal that is electrically connected to the second capacitor plate.

In another embodiment, the power transformer includes a first power transformer terminal and a second power transformer terminal.

In another embodiment, the analog resonator system includes a first output terminal and a second output terminal. The first capacitor plate terminal and the first power transformer terminal are electrically connected to the first output terminal, and the second capacitor plate terminal and the second power transformer terminal are electrically connected to the second output terminal.

In another embodiment, the analog resonator system is configured for use with analog PEMF therapy and/or an analog PEMF therapy device that is electrically connected to the first output terminal and to the second output terminal for receiving the electromagnetic energy generated by the analog resonator system.

In another aspect, the present invention is embodied by an analog PEMF therapy device including a capacitor assembly having a first capacitor plate formed from a first conductive material, a second capacitor plate formed from a second conductive material, and a dielectric insulator plate separating the first capacitor plate and the second capacitor plate. The analog PEMF therapy device further includes a power transformer for supplying electrical potential to the capacitor assembly. The analog PEMF therapy device further includes a bulb electrically connected to the capacitor assembly and the power transformer. The analog PEMF therapy device further includes a base electrically connected to the capacitor assembly and the power transformer.

In one embodiment of the analog PEMF therapy device, the first conductive material is a copper (Cu) metal material, and the second conductive material is an aluminum (Al) metal material.

In another embodiment, the capacitor assembly and the power transformer produce continuous, randomized electromagnetic energy wave forms.

In another embodiment, the power transformer comprises a neon sign transformer for supplying from about 12,000 volts to about 15,000 volts of the electrical potential to the capacitor assembly.

In another embodiment, the analog PEMF therapy device further includes a fan for providing cooling air to the capacitor assembly, and the capacitor assembly further includes at least one cooling air duct for directing the cooling air to the first capacitor plate and/or to the second capacitor plate.

In another aspect, the present invention is embodied by a method for generating electromagnetic energy for analog PEMF therapy. The method includes providing a resonator system including a capacitor assembly and a power transformer. The method further includes providing the capacitor assembly with a first capacitor plate formed from a first conductive material and a second capacitor plate formed from a second conductive material that is dissimilar from the first conductive material. The method further includes supplying electrical potential from the power transformer to the first capacitor plate and to the second capacitor plate. The method further includes electrically connecting an analog PEMF therapy device between the first capacitor plate and the power transformer, and between the second capacitor plate and the power transformer. The method further includes using the resonator system to produce continuous, randomized electromagnetic energy wave forms for the analog PEMF therapy device.

In one embodiment of the method, the first conductive material is a copper (Cu) metal material, and the second conductive material is an aluminum (Al) metal material.

In another embodiment, the first capacitor plate has a first capacitor plate terminal and the second capacitor plate has a second capacitor plate terminal. The power transformer has a first power transformer terminal and a second power transformer terminal. The resonator system further includes a first output terminal and a second output terminal. The first output terminal is electrically connected between the first capacitor plate terminal and the first power transformer terminal, and the second output terminal is electrically connected between the second capacitor plate terminal and the second power transformer terminal.

Additional aspects, objects, features and advantages of the present invention will be made apparent or will be readily understood and appreciated by those skilled in the relevant art, as exemplary embodiments of the invention shown in the accompanying drawing figures are described in greater detail hereinafter. It is intended that all such aspects, objects, features and advantages of the invention envisioned by this disclosure of exemplary embodiments be encompassed by the appended claims given their broadest reasonable interpretation consistent with this disclosure from the viewpoint of one of ordinary skill in the art. Consequently, the various terms used in this disclosure should be construed according to their ordinary and customary meaning as understood by one of ordinary skill in the art at the time of this invention. The aspects, objects, features and advantages of the invention, as well as others not expressly disclosed, may be accomplished by one or more of the exemplary embodiments described hereinafter and shown in the accompanying drawing figures, as well as others that are not expressly described and shown herein. However, it should be appreciated that the exemplary embodiments and drawing figures are merely illustrative of the invention and its various forms, and that many modifications, changes, revisions and substitutions may be made to any of the exemplary embodiments without departing from the general concepts of the invention given it broadest reasonable interpretation and proper construction.

BRIEF DESCRIPTION OF THE DRAWING FIGURES

The aforementioned aspects, objects, features and advantages of the present invention, as well as the exemplary embodiments of the invention, will be more fully understood and appreciated when considered in conjunction with the accompanying drawing figures, in which like reference characters designate the same or similar parts throughout the several views.

DETAILED DESCRIPTION OF EXEMPLARY EMBODIMENTS OF THE INVENTION

Figure 1:
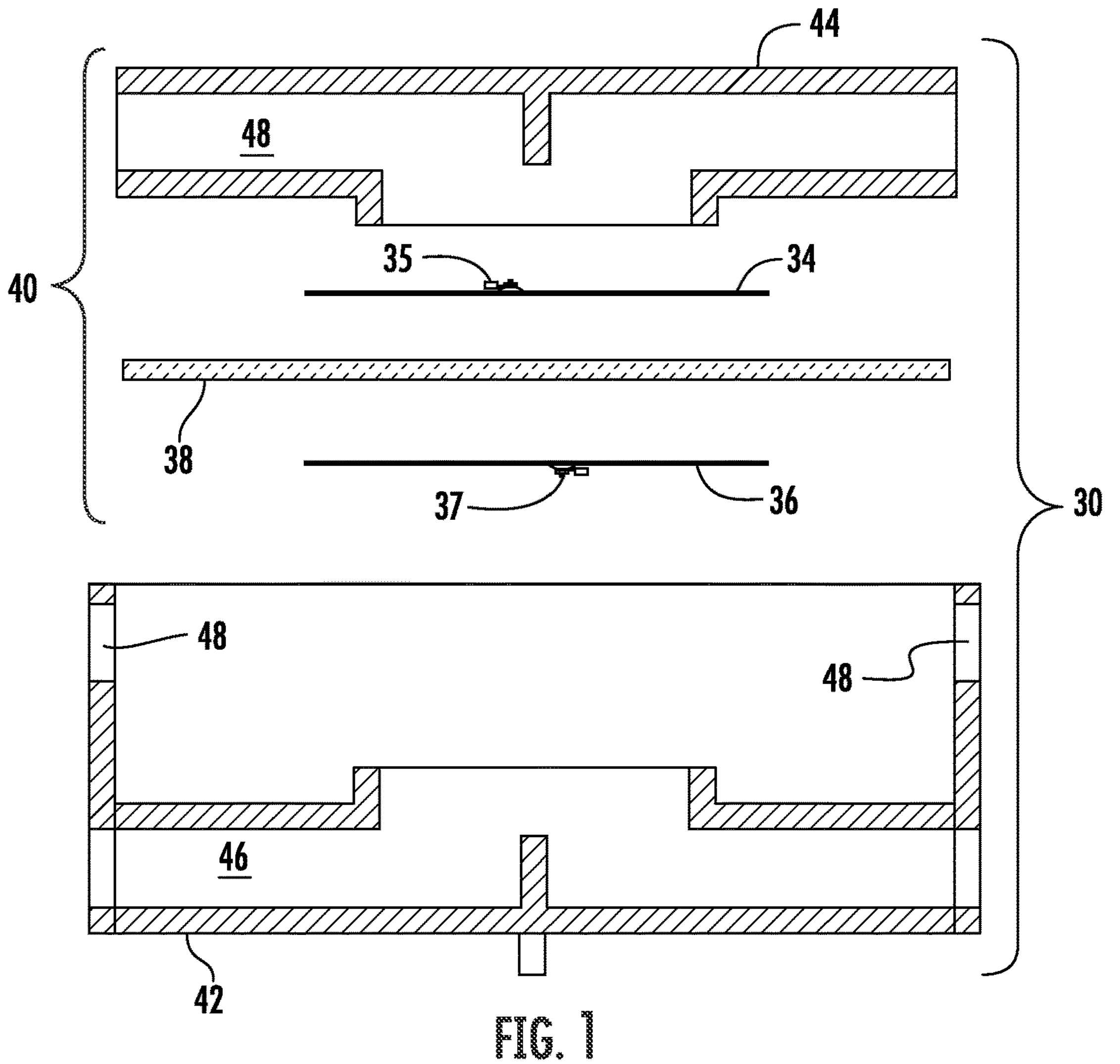
FIG. 1 is a sectioned elevation view showing a capacitor assembly of an analog resonator system for generating electromagnetic energy according to an exemplary embodiment of the present invention with the capacitor assembly shown in an exploded configuration.

The following is a detailed description of exemplary embodiments of a resonator system configured for analog PEMF therapy and for an analog PEMF therapy device. In the exemplary embodiments, the present invention is an analog resonance transformer, also referred to herein as an analog resonator system, for generating electromagnetic energy utilized in analog PEMF therapy and with an analog PEMF therapy device. In particular, the present invention is an analog resonator system for generating a wide spectrum of continuous, randomized electromagnetic energy wave forms for analog PEMF therapy and for an analog PEMF therapy device.

Exemplary embodiments of the present invention are described more fully hereinafter with reference to this detailed description and the accompanying drawing figures. The exemplary embodiments show and describe an analog resonance transformer, resonator or resonator system configured for analog PEMF therapy and for use with an analog PEMF therapy device. However, it is not intended for the present invention to be limited in any manner by the exemplary embodiments shown and described herein. Instead, it is expected the present invention will be given the broadest reasonable interpretation and construction consistent with this disclosure. Furthermore, unless a specific interpretation, definition or construction is expressly provided, the exemplary embodiments illustrated herein, and the various terms used herein should be given their ordinary and customary meanings as would be understood by a person of ordinary skill in the art at the time of the invention.

In one aspect, the present invention is embodied by an analog resonance transformer, resonator or resonator system, indicated generally herein by reference character 20, for generating electromagnetic energy. The analog resonator system 20 includes a capacitor assembly, indicated generally herein by reference character 30, and a power transformer, indicated generally herein by reference character 50. The power transformer 50 provides electrical potential to the capacitor assembly 30. The power transformer supplies electrical potential to the capacitor assembly 30 and the capacitor assembly 30 stores an electrical charge (i.e., capacitance) of the electrical potential in a conventional manner well known and understood by those skilled in the art.

Figure 2:
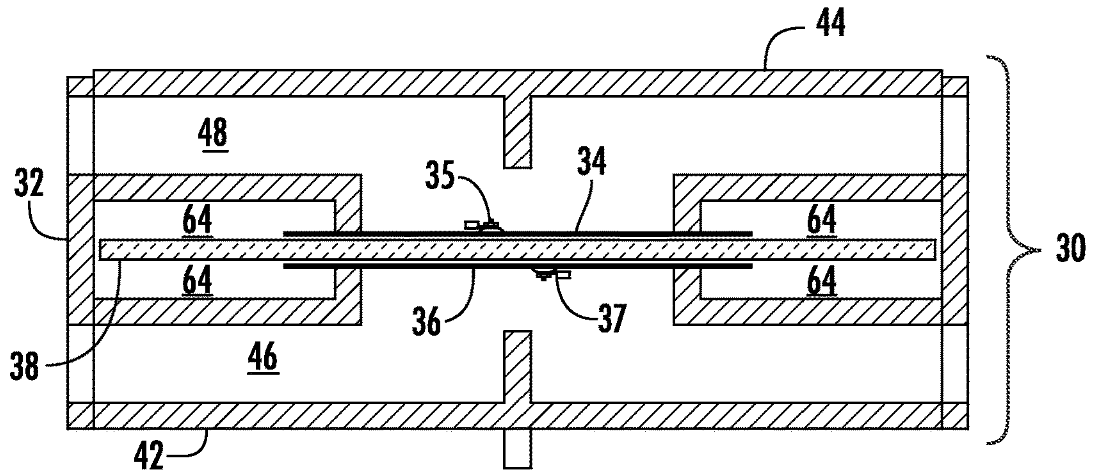
FIG. 2 is a sectioned elevation view showing the capacitor assembly of FIG. 1 in an assembled configuration.
Figure 3:
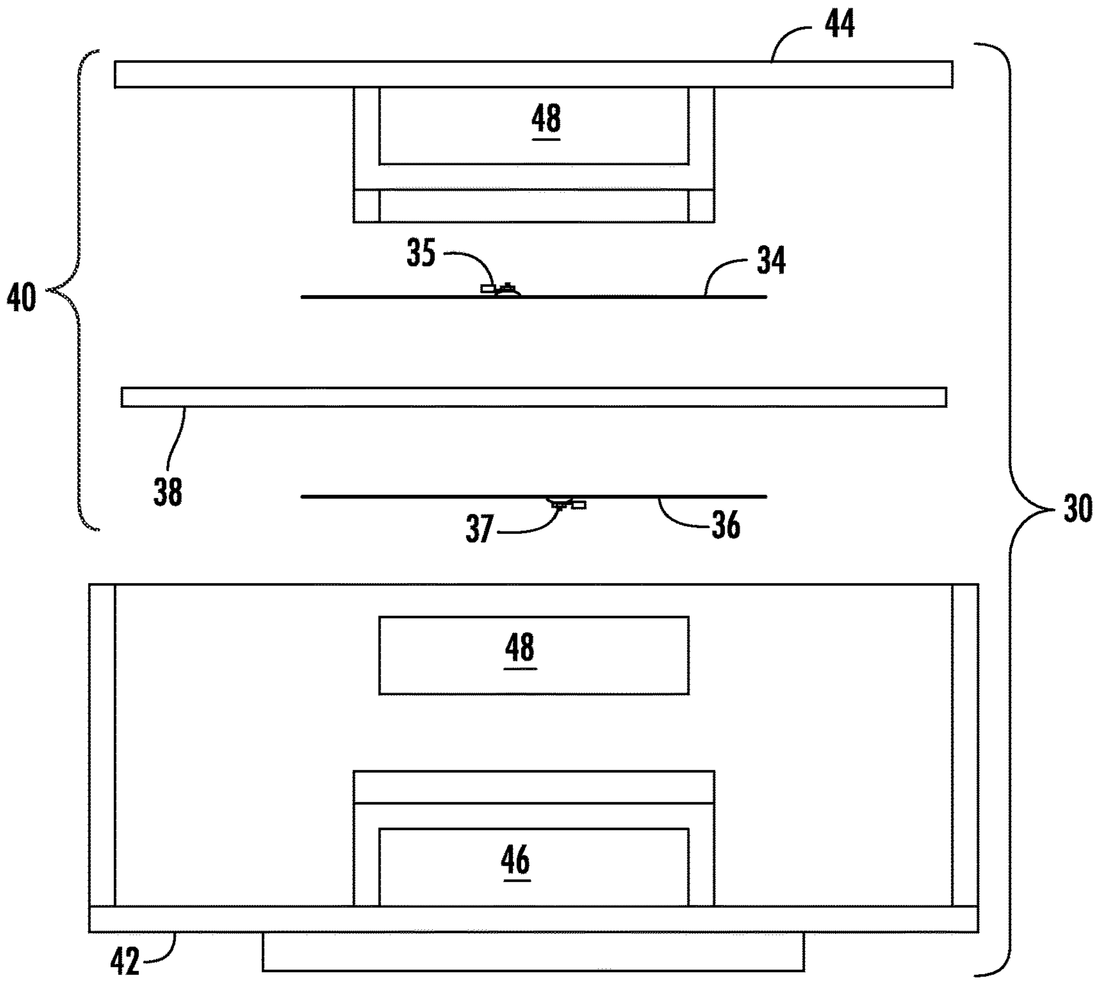
FIG. 3 is an end view showing the capacitor assembly of FIG. 1 in an exploded configuration.
Figure 4:
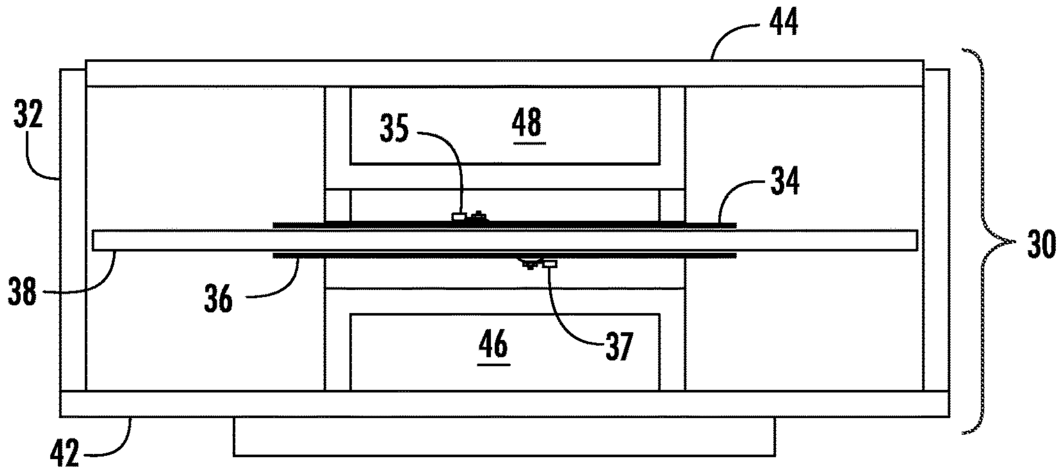
FIG. 4 is an end view showing the capacitor assembly of FIG. 1 in an assembled configuration.

FIGS. 1-4 show the capacitor assembly 30 of the analog resonator system 20 in greater detail. FIG. 1 is an elevation view showing the capacitor assembly 30 in an exploded configuration, while FIG. 2 is an elevation view showing the capacitor assembly 30 of FIG. 1 n an assembled configuration. FIG. 3 is an end view showing the capacitor assembly 30 of FIG. 1 in an exploded configuration, while FIG. 4 is an end view showing the capacitor assembly 30 of FIG. 1 in an assembled configuration.

The capacitor assembly 30 comprises a housing 32 configured for containing the components of the capacitor assembly 30. In particular, the housing 32 of the capacitor assembly 30 is configured to house a first electrode in the form of a first capacitor plate 34 and a second electrode in the form of a second capacitor plate 36. The first capacitor plate 34 and the second capacitor plate 36 are separated by a dielectric insulator plate 38. The first capacitor plate 34 and the second capacitor plate 36 are each made of a conductive material, such as metal. In one embodiment, the first capacitor plate 34 is made of a first metal material and the second capacitor plate 36 is made of a second metal material that is different than, or dissimilar from, the first metal material. Consequently, the capacitor assembly 30 may be referred to as bi-metallic.

In an advantageous embodiment, the first capacitor plate 34 is made of a copper (Cu) metal material and the second capacitor plate 36 is made of an aluminum (Al) metal material. Regardless, the first capacitor plate 34 and the second capacitor plate 36 are each formed as a relatively thin, elongate sheet having a length wise dimension (length) of at least about 7 inches and a width wise dimension (width) of at least about 5 inches. A depth wise dimension (thickness) of the first capacitor plate 34 and the second capacitor plate 36 is preferably between about ⅛ inches and about $^3/_{16}$ inches.

In an advantageous embodiment, the dielectric insulator plate 38 is made of a plastic or glass material. The dielectric insulator plate 38 may be opaque, translucent or semi-transparent, but preferably is substantially transparent. The dielectric insulator plate 38 is likewise formed as a relatively thin, elongate sheet having a length wise dimension (length) of at least about 10 inches, a width wise dimension (width) of at least about 8 inches, and a depth wise dimension (thickness) of between about ⅛ inches and about $^3/_{16}$ inches. Consequently, the dielectric insulator plate 38 has a surface area (length times width) that is relatively larger than the surface area (length times width) of the first capacitor plate 34 and the second capacitor plate 36.

The first capacitor plate 34 has a first capacitor plate terminal 35 for electrically connecting the first capacitor plate 34 to the power transformer 50, as will be described in greater detail hereafter. Similarly, the second capacitor plate 36 has a second capacitor plate terminal 37 for electrically connecting the second capacitor plate 36 to the power transformer 50, as will be described in greater detail hereafter. As will be readily apparent to those skilled in the art, the dielectric insulator plate 38 is not electrically connected to the first capacitor plate 34, or to the second capacitor plate 36, or to the power transformer 50. Instead, the dielectric insulator plate restricts the transfer (conduction) of electrical potential between the first capacitor plate 34 and the second capacitor plate 36. Consequently, an electrical charge (i.e., capacitance) accumulates on the capacitor assembly 30 in a known manner.

The housing 32 comprises a lower portion 42 and an upper portion 44. The lower portion 42 of the housing 32 is configured (i.e., sized and shaped) to receive the upper portion 44 therein, while the upper portion 44 of the housing 32 is configured (i.e., sized and shaped) to be received within the lower portion 42. Preferably, the first capacitor plate 34, the second capacitor plate 36 and the dielectric insulator plate 38 are assembled together with the upper portion 44 of the housing 32 in a subassembly 40 that is received within the lower portion 42 of the housing 32. As a result, the subassembly 40 can be readily removed from the lower portion 42 of the housing 32 to allow for periodic cleaning, service, repair or replacement of the components of the subassembly 40 of the capacitor assembly 30. In particular for periodic cleaning, service, repair or replacement of the first capacitor plate 34, the second capacitor plate 36 and/or the dielectric separator plate 38

In an advantageous embodiment, the lower portion 42 of the housing 32 and the upper portion 44 of the housing 32 are configured (i.e., sized and shaped) to engage in a sealing manner such that the lower portion 42 and the upper portion 44 of the capacitor assembly 30 form an essentially airtight housing 32 in the assembled configuration. The lower portion 42 of the housing 32 defines a lower air duct 46 in the form of a length wise through passage that extends between the opposed ends of the capacitor assembly 30. Likewise, the upper portion 44 of the housing 32 defines an upper air duct 48 in the form of a length wise through passage that extends between the opposed ends of the capacitor assembly 30. As will be described hereafter, the air duct 46 allows airflow through the lower portion 42 of the housing 32 to cool the second capacitor plate 36, while the air duct 48 allows airflow through the upper portion 44 of the housing 32 to cool the first capacitor plate 34 with the housing 32 in the assembled configuration.

Figure 5:
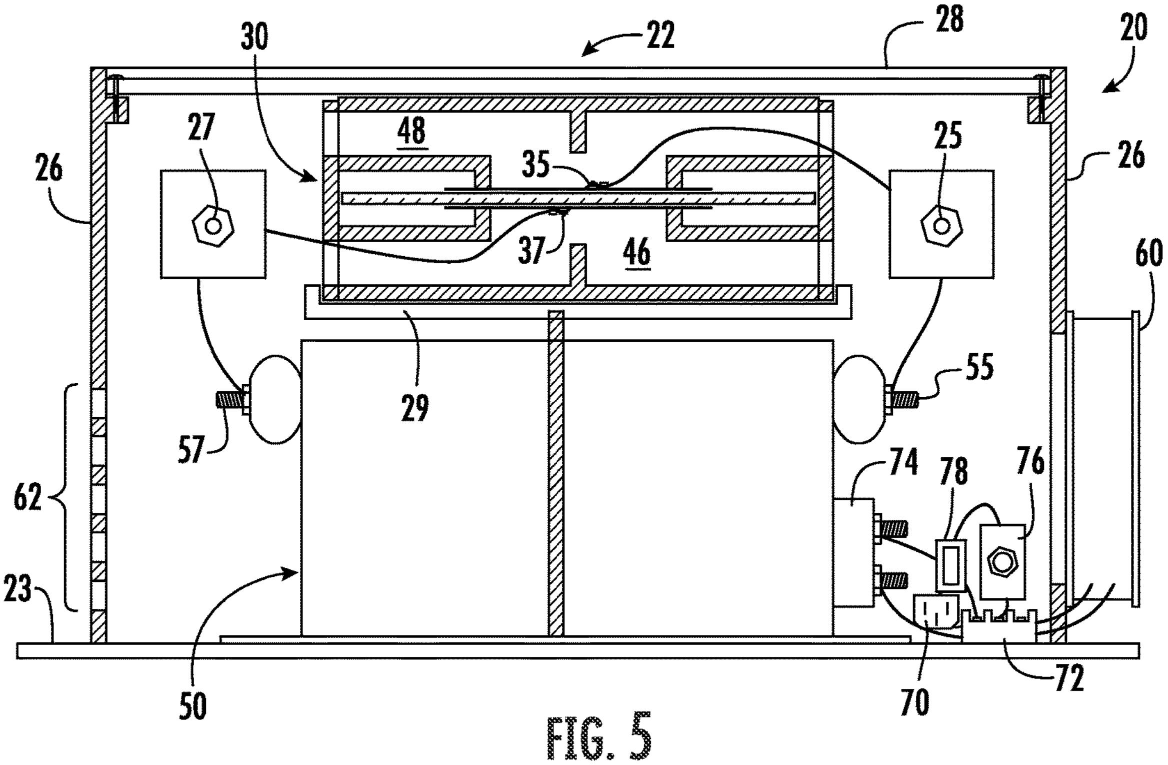
FIG. 5 is a partially sectioned elevation view showing an analog resonator system for generating electromagnetic energy according to an exemplary embodiment of the present invention.
Figure 6:
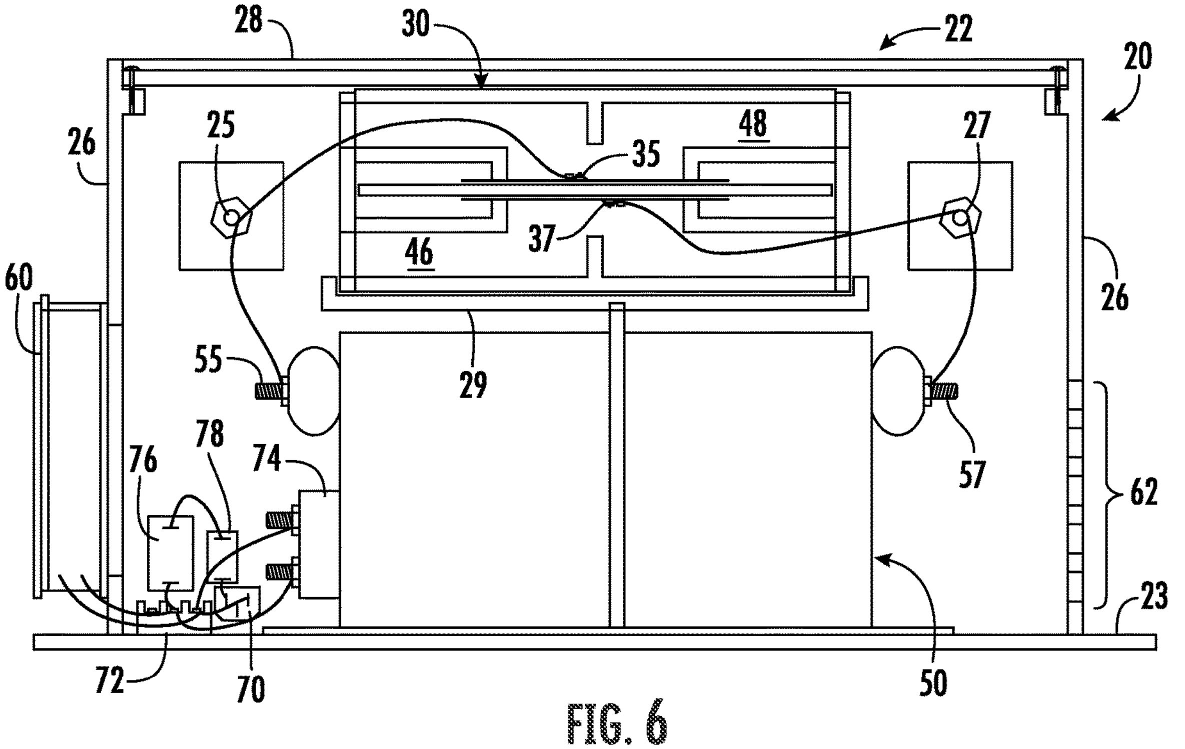
FIG. 6 is an elevation view showing an interior of the analog resonator system of FIG. 5.
Figure 7:
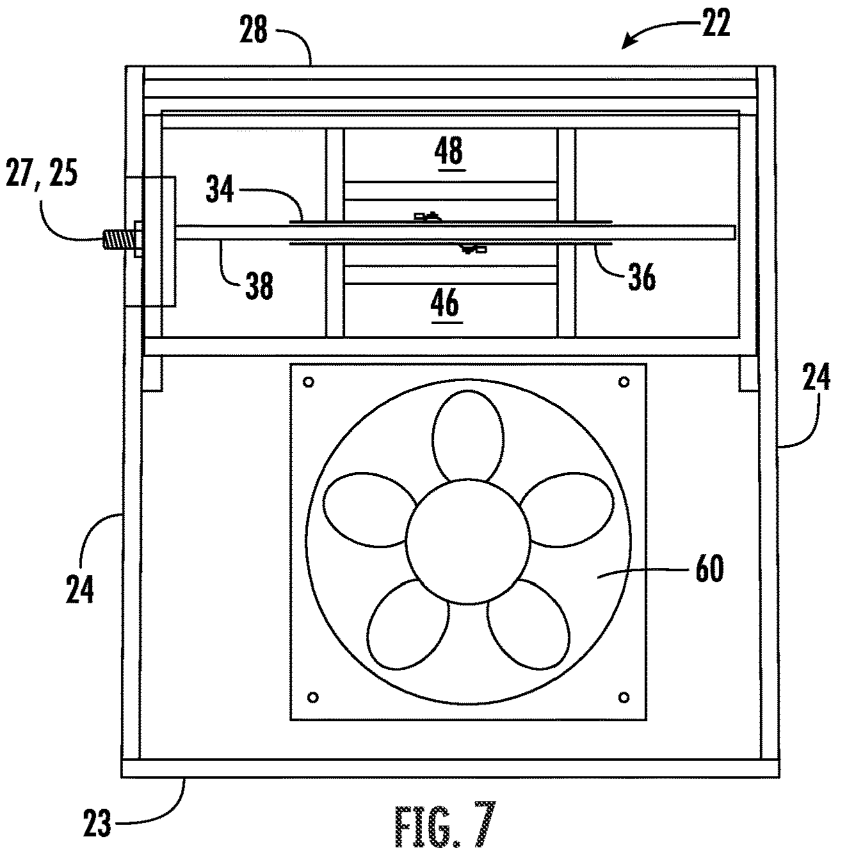
FIG. 7 is a right-hand end view of the analog resonator system of FIG. 5.
Figure 8:
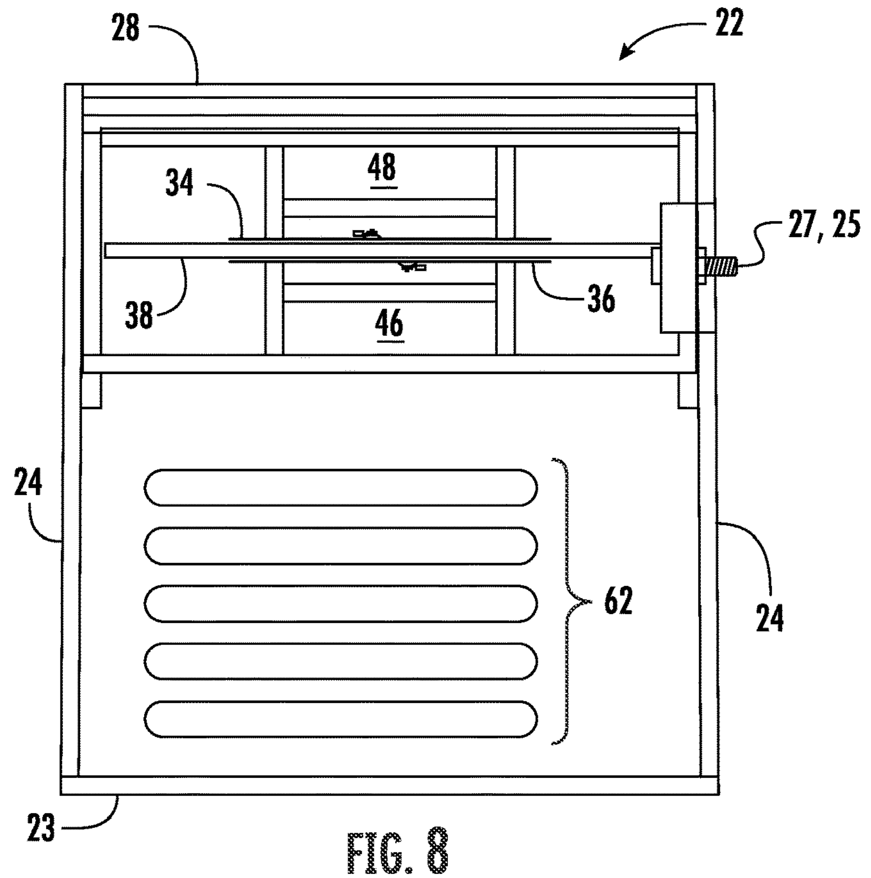
FIG. 8 is a left-hand end view of the analog resonator system of FIG. 5.
Figure 9:
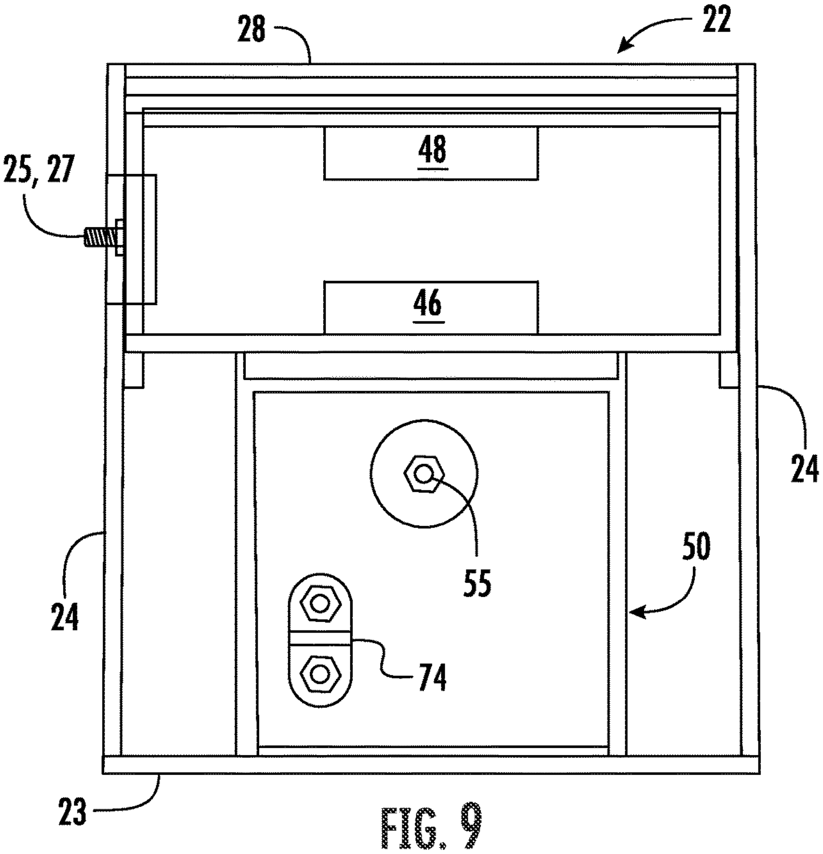
FIG. 9 is an end view showing an interior of the analog resonator system of FIG. 5.
Figure 10:
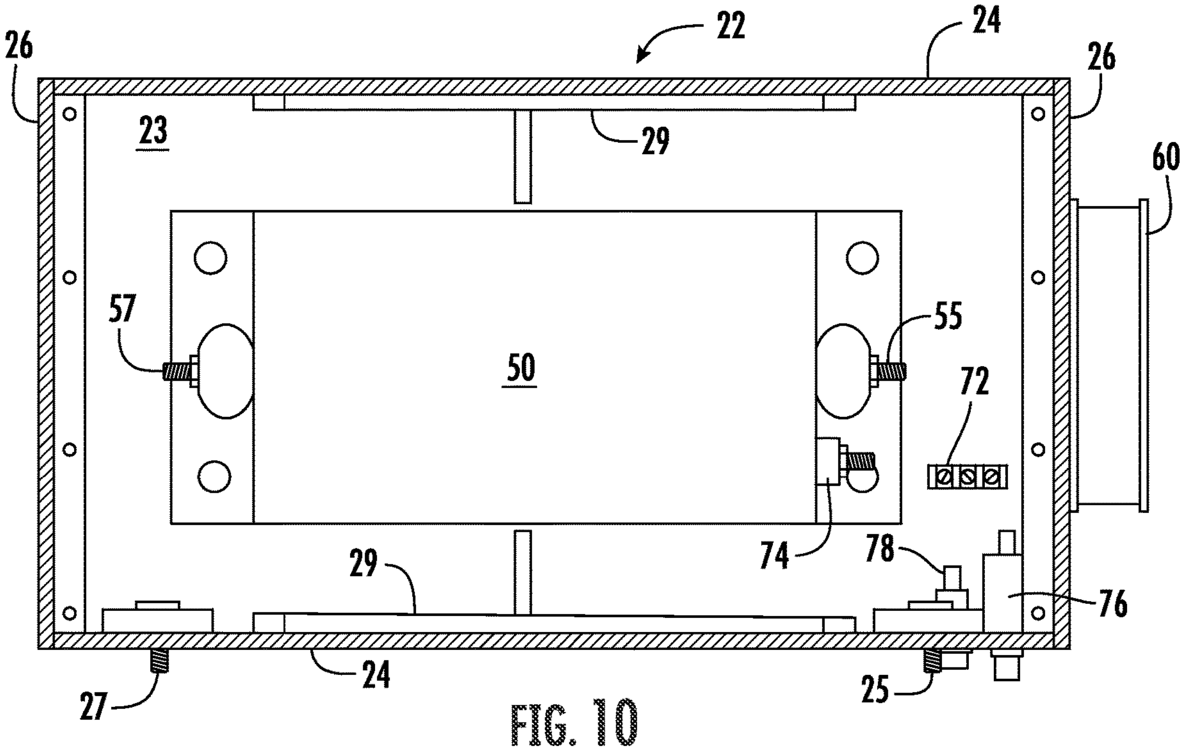
FIG. 10 is a partially sectioned plan view showing an interior of the analog resonator system of FIG. 5.

FIGS. 5-10 show the analog resonator system 20, also referred to herein as an analog resonance transformer or analog resonator, for generating electromagnetic energy according to an exemplary embodiment of the present invention. FIG. 5 is a partially sectioned elevation view showing the analog resonator system 20. FIG. 6 is an elevation view showing an interior of the analog resonator system 20 of FIG. 5. FIG. 7 is a right-hand end view of the analog resonator system 20 of FIG. 5. FIG. 8 is a left-hand end view of the resonator system 20 of FIG. 5. FIG. 9 is an end view showing an interior of the analog resonator system 20 of FIG. 5. FIG. 10 is a partially sectioned plan view showing an interior of the resonator system 20 of FIG. 5.

The power transformer 50 and the capacitor assembly 30 are both contained within a box-like housing 22 of the analog resonator system 20. Housing 22 comprises a base 23, opposed side walls 24, opposed end walls 26 and a removable cover 28. Cover 28 is removable to provide access to housing 22 to allow for periodic cleaning, service, repair or replacement of the components of the resonator system 50, namely the capacitor assembly 30 and the power transformer 50. If desired, the housing 22 may further comprise a cradle 29 for removably supporting the capacitor assembly 30 within the housing 22 of the resonator system 20. An electrically conductive tap, post, terminal or the like in the form of a first output terminal 25 and an electrically conductive tap, post, terminal or the like in the form of a second output terminal 27 are disposed on housing 22. The first and second output terminals 25, 27 are provided on the exterior of the housing 22 of the resonator system 20 for convenient connection to an analog PEMF therapy device. The first and second output terminals 25, 27 may be located anywhere on housing 22. In an advantageous embodiment shown herein, the output terminals 25, 27 are disposed on one of the opposed side walls 24. However, the output terminals 25, 27 may be located on opposite side walls 24, or alternatively, on one or both of the opposed end walls 26. Housing 22 may be made of any suitable material, but preferably is made of an insulating non-conductive material, such as plastic.

As shown herein, the power transformer 50 has a high voltage first power transformer terminal 55 that is in electrical communication with the first capacitor plate terminal 35 and a high voltage second power transformer terminal 57 that is in electrical communication with the second capacitor plate terminal 37. The first power transformer terminal 55 is electrically connected to the first capacitor plate terminal 35 through the first output terminal 25 provided on housing 22. Similarly, the second power transformer terminal 57 is electrically connected to the second capacitor plate terminal 37 through the second output terminal 27 provided on the side wall 24 of housing 22. The power transformer 50 may be any suitable apparatus, device or system for providing electrical potential to the capacitor assembly 30. More particularly, the power transformer 50 may be any device for increasing or decreasing the voltage of an alternating current supplied to the first and second capacitor plates 34, 36 of the capacitor assembly 30. In an advantageous embodiment, the power transformer is operable to supply from about 12,000 volts to about 15,000 volts of electric potential to the first capacitor plate 34 and the second capacitor plate 36 of the capacitor assembly 30. In a further advantageous embodiment, the power transformer 50 is a neon sign transformer.

The resonator system 20 further comprises a fan 60 and vent 62 operable for providing forced air cooling to the first capacitor plate 34 and/or to the second capacitor plate 36 of the capacitor assembly 30. The fan 60 and vent 62 cooperate to push (or alternatively, draw) outside ambient air through the housing 32 of the capacitor assembly 30 to cool the first capacitor plate 34 and/or the second capacitor plate 36. More particularly, the fan 60 and the vent 62 simultaneously force cooling air through the lower air duct 46 of the lower portion 42 of the housing 32 to cool the second capacitor plate 36 of the capacitor assembly 30 and through the upper air duct 48 of the upper portion 44 of the housing 32 to cool the first capacitor plate 34 of the capacitor assembly 30. In an advantageous embodiment, the lower portion 42 and the upper portion 44 of the housing 32 of the capacitor assembly 30 define dead-air zones 64 (FIG. 2) that isolate the active opposed outer edges of the first capacitor plate 34 and the second capacitor plate 36 to contain the majority of any ozone produced by the capacitor plates 34, 36. The housing 32 of the capacitor assembly 30 and/or the housing 22 of the analog resonator system 20 may be provided with walls, baffles or similar structure configured for directing the cooling air over the exposed surfaces of the first and second capacitor plates 34, 36. The fan 60 may be positioned at any suitable location on or within the housing 22 of the analog resonator system 20. Preferably, however, the fan 60 is located adjacent one of the opposed end walls 26 of the housing 22, while the vent 62 is located adjacent the other of the opposed end walls 26 so as to maximize the forced air flow through the capacitor assembly 30 of the analog resonator system 20.

The power transformer 50 may be powered by a conventional alternating current (AC) power source (not shown). The analog resonator system 20 may further comprise a power input 70 configured to receive a conventional power adapter cable, cord, plug or the like from the power source. The power input 70 may be electrically connected to a terminal block 72 operable for distributing electrical power to the power transformer 50 through a pair of low voltage power input terminals 74 and/or to the fan 60. The analog resonator system 20 may further comprise a breaker/pilot light 76 and a rocker-type power switch 78 operable for powering on or powering off the analog resonator system 20. The power and distribution components of the analog resonator system 20 operate in a conventional manner well known to those skilled in the art and as such need not be described in greater detail herein.

Figure 11:
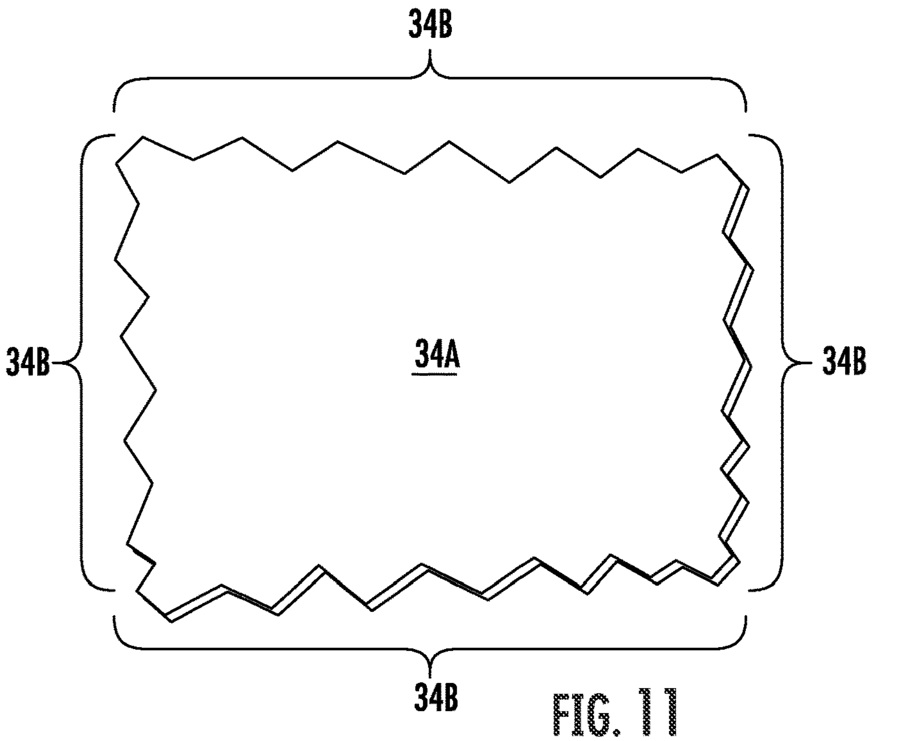
FIG. 11 is a perspective view showing an alternative embodiment of a capacitor plate of the capacitor assembly of FIG. 1 according to the present invention.

FIG. 11 shows an alternative embodiment of a capacitor plate 34A of the capacitor assembly 30 of the analog resonator system 20. Capacitor plate 34A is configured with a series of irregular edges 34B disposed around the periphery of the capacitor plate 34A. The capacitor plate 34A is formed with the irregular edges 34B to produce random wavelengths of the electromagnetic energy analog wave forms according to the variable length and angle of the edge 34B cut into the capacitor plate 34A. It has been found that edges 34B of between about ⅜ inches and about 1 inch in length generate additional wavelengths that increase the electrical noise of the capacitor plate 34A. Consequently, the increased noise of the capacitor plate 34A fills in the frequencies of the wide spectrum of continuous, randomized electromagnetic energy analog wave forms produced by the analog resonator system 20.

The analog resonance transformer, analog resonator or analog resonator system 20 described and shown herein produces a pulsed electromagnetic energy analog frequencies effect without the use of digital electronic pulse synthesizers that have a limited operating range. The analog resonator system 20 comprises a bi-metallic capacitor assembly 30 and a power transformer 50 for supplying electrical potential to the capacitor assembly 30. In advantageous embodiments, the capacitor assembly 30 is constructed with different, or dissimilar, metals in a unique manner and coupled with a neon sign transformer power transformer 50 to produce a desired wide spectrum of continuous, randomized electromagnetic energy analog wave forms particularly well suited for use in analog PEMF therapy and for use with analog PEMF therapy devices.

The capacitor assembly 30 is constructed with a first capacitor plate 34 formed from a copper (CU) metal material and a second capacitor plate 36 formed from an aluminum (Al) metal material separated by a dielectric insulator plate 38 formed from a glass material. The neon sign transformer power transformer 50 supplies from about 12,000 volts to about 15,000 volts to cause the first and second capacitor plates 34, 36 in close proximity to resonate freely at different harmonics and thereby produce essentially "white noise" covering the radio frequencies from about 60 hertz to about 500,000,000 hertz at a relatively low power level. As a result, an analog resonator system 20 according to the present invention provides all of the frequencies that the cellular structure of the human body needs to absorb for optimum cellular operation, while rejecting unwanted frequencies. Conversely, a resonator system that generates discrete frequencies of digital wave forms cannot possibly provide all of the frequencies needed for cellular operation due to the complex structure of the DNA of the human body.

Figure 12:
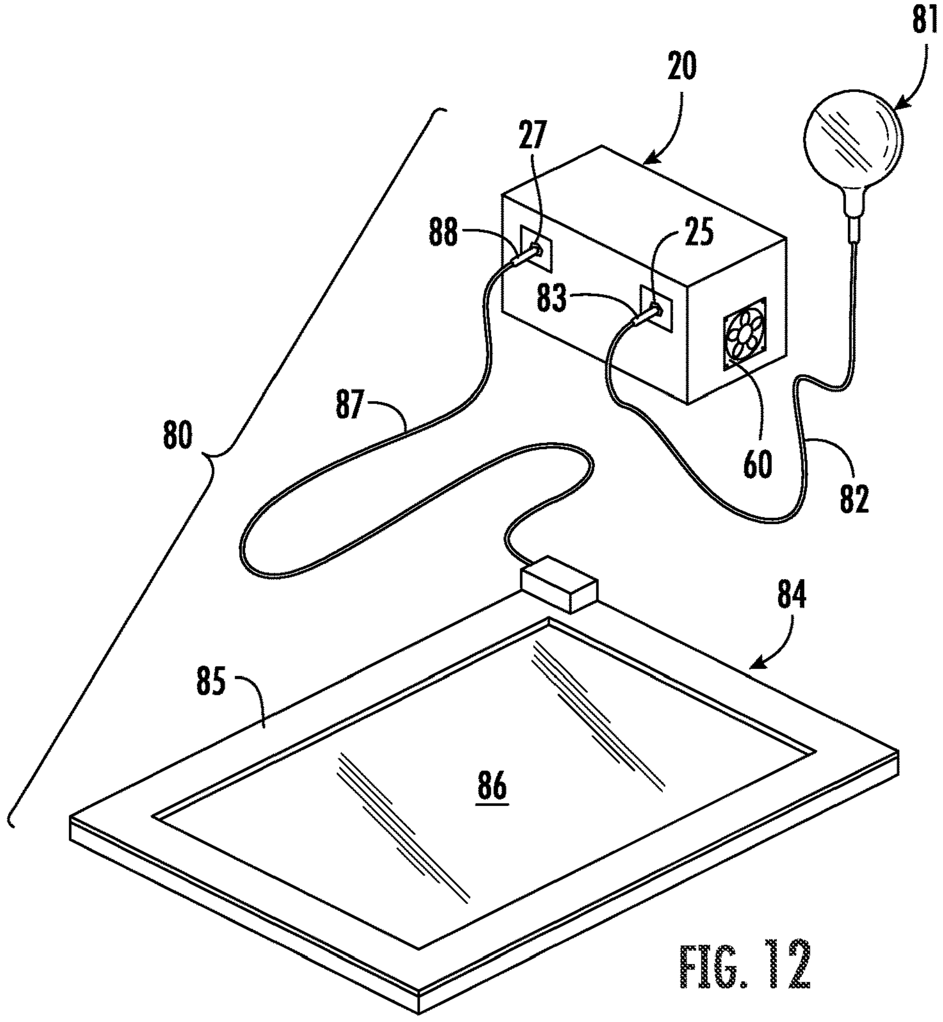
FIG. 12 is an environmental perspective view illustrating an analog PEMF therapy device according to an exemplary embodiment of the present invention.

FIG. 12 shows a conventional analog PEMF therapy device 80 configured for use with the analog resonator system 20 according to an exemplary embodiment of the present invention. The analog PEMF therapy device 80 comprises the analog resonator system 20 containing the capacitor assembly 30, the power transformer 50 and the fan 60 previously described. The analog PEMF therapy device 80 further comprises a rarefied gas bulb 81 formed from a break-resistant glass material. The bulb 81 comprises an electrical cable, cord or the like 82 having a suitable plug, adapter or the like 83 at one end for connection to one of the first and second output terminals 25, 27 provided on the housing 22 of the analog resonator system 20. The analog PEMF therapy device 80 further comprises a base 84 in the form of a generally planar, relatively flat mat. The base 84 may comprise a frame 85, preferably formed from a suitable insulating, non-conducting material, such as hard plastic, configured to enclose and contain the outer edges and underside of an inner panel 86, preferably formed from a hard plastic or glass material. The base 84 further comprise a conductive material, such as a relatively thin sheet of metal foil, such as aluminum foil, (not shown for purpose of clarity) disposed between frame 85 and the inner panel 86. The base 84 further comprises an electrical cable, cord or the like 87 having a suitable plug, adapter or the like 88 at one end for connection to the other of the first and second output terminals 25, 27 provided on the housing 22 of the analog resonator system 20.

In operation, the plug 83 of the bulb 81 of the analog PEMF therapy device 80 is connected to one of the first and second output terminals 25, 27 on the housing 22 of the analog resonator system 20. The plug 88 of the base 84 of the analog PEMF therapy device 80 is connected to the other of the first and second output terminals 25, 27 on the housing 22 of the analog resonator system 20. The analog resonator system 20 is powered from a conventional alternating current (AC) power source (not shown) so that the power transformer 50 supplies electrical potential to the capacitor assembly 30 and the fan 60 provides forced cooling air to the first and second capacitor plates 34, 36 of the capacitor assembly 60. A user (not shown for purposes of clarity) holds the bulb 81 of the analog PEFM therapy device 80 between his/her hands and places his/her body, for example feet, back or legs, onto the base 84 of the analog PEMF therapy device 80. The analog PEMF therapy device 80 including the analog resonator system 20 produce a wide spectrum of continuous, randomized analog wave form frequencies of pulsed electromagnetic energy that pass through the body of the user to provide optimum cellular operation.

Regardless of the foregoing detailed description of exemplary embodiments of the invention, the optimum configuration of the article of manufacture, apparatus, device or system, and the manner of use, operation and steps of the associated methods, as well as reasonable equivalents thereof, are deemed to be readily apparent and understood by those skilled in the art. Accordingly, equivalent relationships to those shown in the accompanying drawing figures and described in the written description are intended to be encompassed by the present invention given the broadest reasonable interpretation and construction of the appended claims, the foregoing written description and the drawing figures being considered as merely illustrative of the general concepts and principles of the invention. Furthermore, as numerous modifications and changes will readily occur to those skilled in the art, the invention is not intended to be limited to the specific configuration, construction, materials, manner of use and operation of the exemplary embodiments shown and described herein. Instead, all reasonably predictable and suitable equivalents and obvious modifications to the invention should be construed as falling within the scope of the invention as defined by the appended claims given their broadest reasonable interpretation and construction to one of ordinary skill in the art within the context of the foregoing written description and accompanying drawing figures.

That which is claimed is:

1. An analog resonator system for generating electromagnetic energy, comprising:

a capacitor assembly including a first capacitor plate, a second capacitor plate and a dielectric insulator plate separating the first capacitor plate and the second capacitor plate; and a power transformer operable for supplying electrical potential to the first capacitor plate and to the second capacitor plate;

wherein the first capacitor plate and the second capacitor plate are each electrically connected to the power transformer; and wherein the first capacitor plate is formed from a first metal material and the second capacitor plate is formed from a second metal material that is different from the first metal material.

2. The analog resonator system according to claim 1, wherein the first capacitor plate of the capacitor assembly is formed of a copper (Cu) metal material and the second capacitor plate of the capacitor assembly is formed of an aluminum (Al) metal material.

3. The analog resonator system according to claim 1, wherein the capacitor assembly and the power transformer produce continuous, randomized analog wave forms of the electromagnetic energy generated by the resonator system.

4. The analog resonator system according to claim 1, wherein the power transformer comprises a neon sign transformer for supplying from 12,000 volts to 15,000 volts of the electrical potential to the capacitor assembly.

5. The analog resonator system according to claim 1, further comprising a fan for providing forced cooling air to the capacitor assembly, and wherein the capacitor assembly further comprises at least one cooling air duct for directing the forced cooling air to the first capacitor plate and/or to the second capacitor plate.

6. The analog resonator system according to claim 1, wherein the capacitor assembly further comprises a first housing for containing the capacitor assembly, and wherein the analog resonator system further comprises a second housing for containing the capacitor assembly and the power transformer.

7. The analog resonator system according to claim 6, wherein the first housing of the capacitor assembly is contained within and is removable from the second housing.

8. The analog resonator system according to claim 1, wherein the analog resonator system further comprises a first output terminal and a second output terminal, and wherein the first output terminal is electrically connected between the power transformer and the first capacitor plate, and wherein the second output terminal is electrically connected between the power transformer and the second capacitor plate.

9. The analog resonator system according to claim 8, wherein the first metal material and the second metal material resonate at different harmonics, and wherein the analog resonator system is configured for use with analog PEMF therapy and/or an analog PEMF therapy device that is electrically connected to the first output terminal and to the second output terminal for receiving the electromagnetic energy generated by the analog resonator system.

10. The analog resonator system according to claim 1, wherein the capacitor assembly further comprises a first capacitor plate terminal electrically connected to the first capacitor plate and a second capacitor plate terminal electrically connected to the second capacitor plate.

11. The analog resonator system according to claim 10, wherein the power transformer further comprises a first power transformer terminal and a second power transformer terminal.

12. The analog resonator system according to claim 11, wherein the analog resonator system further comprises a first output terminal and a second output terminal, and wherein the first capacitor plate terminal and the first power transformer terminal are electrically connected to the first output terminal, and wherein the second capacitor plate terminal and the second power transformer terminal are electrically connected to the second output terminal.

13. An analog PEMF therapy device, comprising:

a capacitor assembly having a first capacitor plate formed from a first conductive material, a second capacitor plate formed from a second conductive material, and a dielectric insulator plate separating the first capacitor plate and the second capacitor plate, the first conductive material and the second conductive material being different conductive materials that resonate at different harmonics;

a power transformer for supplying electrical potential to the capacitor assembly;

a bulb electrically connected to the capacitor assembly and electrically connected the power transformer; and a base electrically connected to the capacitor assembly and electrically connected to the power transformer.

14. The analog PEMF therapy device according to claim 13, wherein the first conductive material is a copper (Cu) metal material and the second conductive material is an aluminum (Al) metal material.

15. The analog PEMF therapy device according to claim 13, wherein the capacitor assembly and the power transformer produce continuous, randomized analog wave forms of electromagnetic energy.

16. The analog PEMF therapy device according to claim 13, wherein the power transformer comprises a neon sign transformer for supplying from 12,000 volts to 15,000 volts of the electrical potential to the capacitor assembly.

17. The analog PEMF therapy device according to claim 13, further comprising a fan for providing forced cooling air to the capacitor assembly, and wherein the capacitor assembly further comprises at least one cooling air duct for directing the forced cooling air to the first capacitor plate and/or to the second capacitor plate.

18. A method for generating electromagnetic energy for analog PEMF therapy, comprising:

providing an analog resonator system comprising a capacitor assembly and a power transformer;

providing the capacitor assembly with a first capacitor plate formed from a first conductive material and a second capacitor plate formed from a second conductive material that is different from the first conductive material;

supplying electrical potential from the power transformer to the first capacitor plate and to the second capacitor plate;

electrically connecting an analog PEMF therapy device between the first capacitor plate and the power transformer and between the second capacitor plate and the power transformer; and using the analog resonator system to produce continuous, randomized analog wave forms of the electromagnetic energy for the analog PEMF therapy device.

19. The method according to claim 18, wherein the first conductive material is a copper (Cu) metal material and the second conductive material is an aluminum (Al) metal material.

20. The method according to claim 18, wherein the first capacitor plate has a first capacitor plate terminal and the second capacitor plate has a second capacitor plate terminal;

wherein the power transformer has a first power transformer terminal and a second power transformer terminal;

wherein the analog resonator system further comprises a first output terminal and a second output terminal; and wherein the first output terminal is electrically connected between the first capacitor plate terminal and the first power transformer terminal, and wherein the second output terminal is electrically connected between the second capacitor plate terminal and the second power transformer terminal.

* * * * *